(12) United States Patent
Whitfield et al.

(10) Patent No.: US 9,827,205 B2
(45) Date of Patent: *Nov. 28, 2017

(54) DRY POWDER FIBRIN SEALANT

(75) Inventors: Nicola Whitfield, Nottingham (GB); Jaap Koopman, Leiden (NL); Jos Grimbergen, Leiden (NL)

(73) Assignees: Mallinckrodt Pharma IP Trading D.A.C., Dublin (IE); Quadrant Drug Delivery Limited, Nottingham (GB)

( * ) Notice: Subject to any disclaimer, the term of this patent is extended or adjusted under 35 U.S.C. 154(b) by 1132 days.

This patent is subject to a terminal disclaimer.

(21) Appl. No.: 12/636,718

(22) Filed: Dec. 12, 2009

(65) Prior Publication Data
US 2010/0150900 A1    Jun. 17, 2010

Related U.S. Application Data

(60) Provisional application No. 61/122,063, filed on Dec. 12, 2008.

(51) Int. Cl.
| | | |
|---|---|---|
| *A61K 38/48* | (2006.01) | |
| *A61K 9/14* | (2006.01) | |
| *A61K 38/36* | (2006.01) | |
| *A61K 9/50* | (2006.01) | |
| *A61K 9/16* | (2006.01) | |

(52) U.S. Cl.
CPC .......... *A61K 9/5084* (2013.01); *A61K 38/363* (2013.01); *A61K 38/4833* (2013.01); *C12Y 304/21005* (2013.01); *A61K 9/1623* (2013.01)

(58) Field of Classification Search
None
See application file for complete search history.

(56) References Cited

U.S. PATENT DOCUMENTS

| | | |
|---|---|---|
| 4,427,650 A | 1/1984 | Stroetmann |
| 4,427,651 A | 1/1984 | Stroetmann |
| 4,442,655 A | 4/1984 | Stroetmann |
| 4,752,466 A | 6/1988 | Saferstein |
| 4,891,319 A | 1/1990 | Roser |
| 5,518,709 A | 5/1996 | Sutton et al. |
| 5,621,094 A | 4/1997 | Roser et al. |
| 5,741,478 A | 4/1998 | Osborne et al. |
| 5,951,531 A | 9/1999 | Ferdman et al. |
| 5,955,108 A | 9/1999 | Sutton et al. |
| 5,957,848 A | 9/1999 | Sutton et al. |
| 5,993,805 A | 11/1999 | Sutton et al. |
| 6,015,546 A | 1/2000 | Sutton et al. |
| 6,022,525 A | 2/2000 | Sutton et al. |
| 6,051,256 A | 4/2000 | Platz et al. |
| 6,054,122 A | 4/2000 | MacPhee et al. |
| 6,113,948 A | 9/2000 | Heath et al. |
| 6,117,425 A | 9/2000 | MacPhee et al. |
| 6,162,241 A | 12/2000 | Coury et al. |
| 6,183,498 B1 | 2/2001 | Devore et al. |
| 6,258,341 B1 | 7/2001 | Foster et al. |
| 6,290,991 B1 | 9/2001 | Roser et al. |
| 6,309,671 B1 | 10/2001 | Foster et al. |
| 6,331,310 B1 | 12/2001 | Roser et al. |
| 6,344,182 B1 | 2/2002 | Sutton et al. |
| 6,348,186 B1 | 2/2002 | Sutton et al. |
| 6,416,739 B1 | 7/2002 | Rogerson et al. |
| 6,416,741 B1 | 7/2002 | Sutton et al. |
| 6,423,344 B1 | 7/2002 | Platz et al. |
| 6,565,871 B2 | 5/2003 | Roser et al. |
| 6,569,405 B1 | 5/2003 | Sutton et al. |
| 6,582,728 B1 | 6/2003 | Platz et al. |
| 6,589,560 B2 | 7/2003 | Foster et al. |
| 6,592,904 B2 | 7/2003 | Platz et al. |
| 6,623,722 B1 | 9/2003 | Osborne et al. |
| 6,632,648 B1 | 10/2003 | Kampinga et al. |
| 6,709,650 B1 | 3/2004 | Sutton et al. |
| 6,811,792 B2 | 11/2004 | Roser et al. |
| 6,890,512 B2 | 5/2005 | Roser et al. |
| 6,893,657 B2 | 5/2005 | Roser et al. |
| 6,916,911 B1 | 7/2005 | Bar et al. |
| 6,939,530 B2 | 9/2005 | Sutton et al. |
| 6,946,098 B2 | 9/2005 | Miekka et al. |
| 7,056,495 B2 | 6/2006 | Roser et al. |
| RE39,192 E | 7/2006 | MacPhee et al. |
| 7,097,827 B2 | 8/2006 | Platz et al. |
| 7,138,141 B2 | 11/2006 | Platz et al. |
| 7,196,054 B1 | 3/2007 | Drohan et al. |
| 7,229,959 B1 | 6/2007 | Drohan et al. |
| 7,544,177 B2 | 6/2009 | Gertner et al. |

(Continued)

FOREIGN PATENT DOCUMENTS

| | | |
|---|---|---|
| CA | 2199954 | 4/1996 |
| EP | 1 469 740 B1 | 5/2008 |
| WO | WO 96/17633 | 6/1996 |
| WO | WO 98/17257 A1 | 4/1998 |
| WO | WO 2007/022485 A2 | 2/2007 |

OTHER PUBLICATIONS

Bishoff, J.T., et al., "Laparoscopic heminephrectomy using a new fibrin sealant powder," *Urology*, 2003, pp. 1139-1143, vol. 62, No. 6. Abstract Only.

Holcomb, J., et al., "Efficacy of a Dry Fibrin Sealant Dressing for Hemorrhage Control After Ballistic Injury,"*Arch. Surg*, Jan. 1998, pp. 32-35, vol. 133.

"Achieve rapid, pain-free hemostatsis in difficult to reach surgical bleeding wounds," http://www.medafor.com/products/flexitip.html, Nov. 13, 2008.

Grimbergen et al. "Optimization of a new dry powder Fibrin Sealant (Fibrocaps™)" XXth International Fibrinogen Workshop, Venice, Italy, Jul. 10-13, 2008, abstract.

(Continued)

*Primary Examiner* — David J Steadman

(57) ABSTRACT

The invention provides a composition comprising a mixture of first microparticles that comprise fibrinogen and trehalose, and second microparticles that comprise thrombin and trehalose. The invention further provides methods for treating wounds by administering the novel microparticle composition.

25 Claims, 2 Drawing Sheets

(56) References Cited

U.S. PATENT DOCUMENTS

| | | | |
|---|---|---|---|
| 7,572,769 | B2 | 8/2009 | Rapp et al. |
| 7,744,925 | B2 | 6/2010 | Roser et al. |
| 7,780,991 | B2 | 8/2010 | Roser et al. |
| 7,785,631 | B2 | 8/2010 | Roser et al. |
| 2003/0211592 | A1 | 11/2003 | Kampinga et al. |
| 2004/0175328 | A1 | 9/2004 | Sutton et al. |
| 2004/0219206 | A1 | 11/2004 | Roser et al. |
| 2005/0238586 | A1 | 10/2005 | Sutton et al. |
| 2006/0034809 | A1* | 2/2006 | Ho et al. ............ 424/93.7 |
| 2007/0249033 | A1 | 10/2007 | Kampinga et al. |
| 2008/0033331 | A1* | 2/2008 | MacPhee et al. ............ 602/50 |
| 2012/0315305 | A1* | 12/2012 | Koopman et al. ............ 424/400 |

OTHER PUBLICATIONS

Maggos, C. "ProFibrix: Hemostatic Sprinkles" BioCentury, Mar. 26, 2007, pp. A15.

"MPH Mode of Action," http://www.medafor.com/technology/index.html, Nov. 13, 2008.

"QuikClot," http://www.z-medica.com/products/quikclot_granular.asp, Nov. 13, 2008.

"Simple, Effective and Safe for Surgical Applications," http://www.medafor.com/products/arista.html, Nov. 13, 2008.

U.S. Appl. No. 12/827,057, filed Jun. 30, 2010 (Kampinga et al.), entitled "Methods of Terminal Sterilization of Biological Products", now abandoned.

Koopman et al., "FIBROCAPS™: a novel dry powder formulation of fibrin sealant based on pre-mixed blends of fibrinogen and thrombin micro-particles," XVIII$^{th}$ International Fibrinogen Workshop, Chapel Hill, NC (Jul. 17-20, 2004).

Luzley, "The Great Biotechs Awake," The Motley Fool UK Discussion Boards (Nov. 11, 1999). (downloaded Apr. 7, 2013 from http://boards.fool.co.uk/the-great-biotechs-awake-5770599.aspx).

ProFibrix: The Fibrogen Company, Slide Presentation, 2005 Advanced Technology Applications for Combat Casualty Care Conference (2005).

Sibbons et al., "Application of a new dry powder fibrin sealant (FIBROCAPS™) as a topical haemostat in liver injury," XIX$^{th}$ International Fibrinogen Workshop, Guildford, UK (Jun. 23-26, 2006).

Cannon, Bradford et al., "Rate of epithelial regeneration: a clinical method of measurement, and the effect of various agents recommended in the treatment of burns," *Annals of Surgery*, 1943, vol. 117, No. 1, p. 85-92.

Klemm, William R., "Enhanced healing of skin wounds in dogs with systemically and locally administered drugs," *Experientia*, 1967, vol. 23, No. 1, p. 55-57.

\* cited by examiner

DRY POWDER FIBRIN SEALANT

CROSS-REFERENCE TO A RELATED APPLICATION

This application claims the benefit of U.S. provisional application Ser. No. 61/122,063, filed Dec. 12, 2008, which is incorporated herein by reference in its entirety.

FIELD OF THE INVENTION

This invention relates to a dry powder fibrin sealant.

BACKGROUND OF THE INVENTION

WO97/44015 describes a dry powder fibrin sealant based on micro-particles of fibrinogen and thrombin. This has been demonstrated to be an easy-to-use, stable and efficacious topical haemostat. The product can be used immediately, without reconstitution. On contact with aqueous fluid such as blood, the exposed active thrombin immediately converts the exposed fibrinogen into insoluble fibrin polymers.

SUMMARY OF THE INVENTION

The novel fibrin sealant is a blend of spray-dried fibrinogen and thrombin, each of which has been individually co-spray dried with an excipient. A number of excipients have been used in the fibrin sealant formulation to stabilise the active ingredients fibrinogen and thrombin and the physical stability evaluated. In addition, the fibrin sealant formulation has been exposed to electron beam/gamma irradiation or heat sterilisation in order to terminally sterilize the product. The results of the evaluation indicate that trehalose is the most effective excipient in terms of protein protection during stability storage and electron beam exposure. The superior stabilization afforded by the trehalose-based formulations may be attributed to the higher glass transition temperature of trehalose compared to other excipients such as sucrose.

The influence of different parameters on the efficacy of the product was determined in pig liver biopsy models and pig liver resection models. The efficacy of the fibrin sealant powder to stop severely bleeding injuries, with blood loss of >10 ml/min, was enhanced by the opportunity to apply pressure directly after administration of the product. Fibrin sealant powders with a fibrinogen content of at least 4% w/w and a thrombin content of at least 139 IU/g were shown to be effective in stopping severe bleeding. The optimum fibrinogen and thrombin content was ~7.5% w/w and ~400 IU/g, respectively. Fibrinogen and thrombin from 3 different suppliers all performed equally well, demonstrating the robustness of the product. Terminal sterilization of the product using electron beam or gamma irradiation of up to 15 or 25 kGy had no effect on the efficacy of the product and is considered to reduce the risk of bacterial contamination before use. In summary, the invention provides a fibrin sealant product that demonstrates high efficacy at low fibrinogen levels in severely bleeding wounds and can be terminally sterilized using standard irradiation methods.

DESCRIPTION OF PREFERRED EMBODIMENTS

Figure 1:
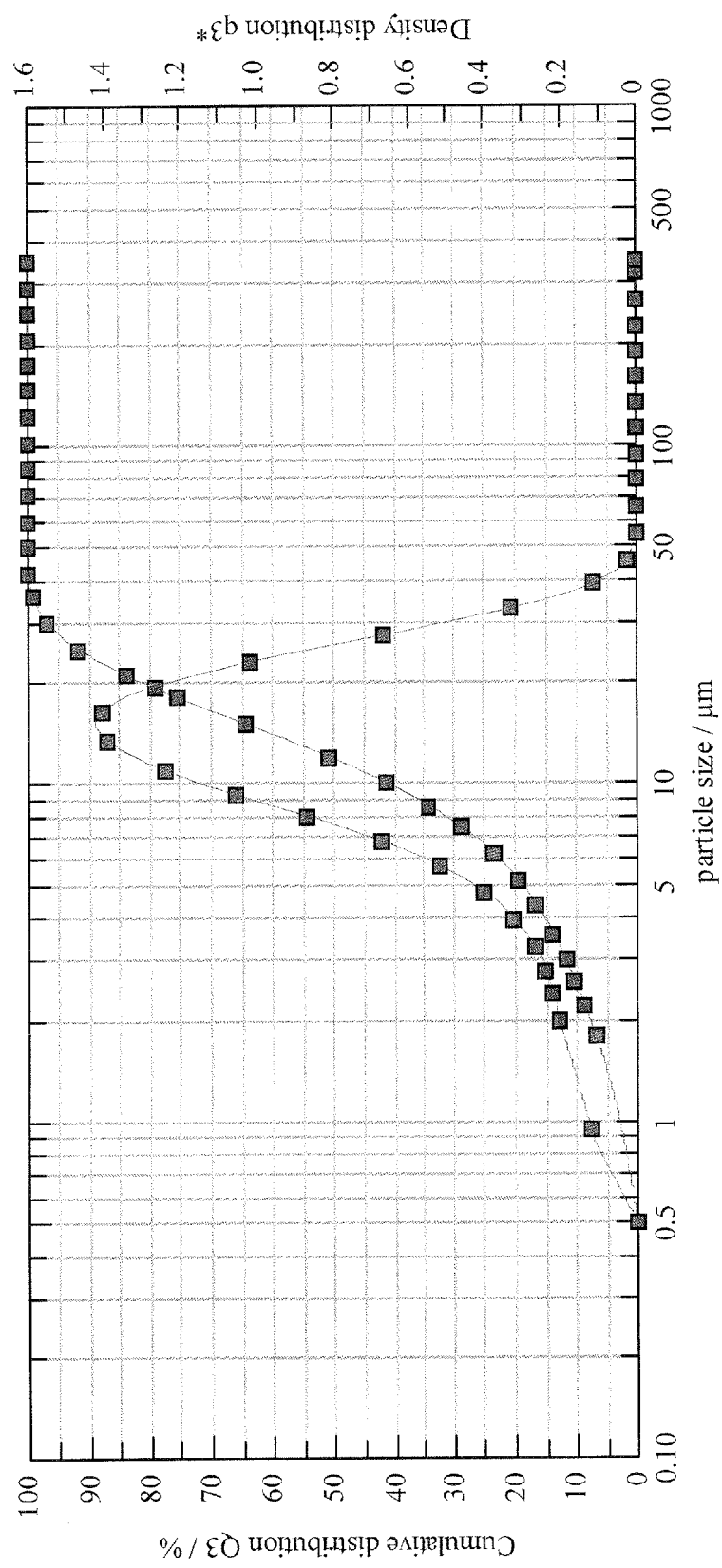
FIG. 1 is a plot of the particle size distribution of spray-dried thrombin:trehalose according to the invention.

Respective fibrinogen-containing and thrombin-containing soluble microparticles can be formulated together, in stable, dry form. This formulation can be subsequently activated, as desired, to give a fibrin sealant that is useful in wound therapy and surgical repair. It can meet the primary objectives of achieving good flow properties, enhanced, effective delivery to the active site, and dissolution only at the site, not in the delivery system.

The content of fibrinogen in the microparticles containing it may be about 0.1 to 50% w/w, preferably about 0.5 to 20 w/w. The content of thrombin in the microparticles containing it may be about 10 to 20,000 IU/g, preferably about 25 to 1,000 IU/g.

Microparticles comprising fibrinogen or thrombin may be prepared by the procedures described in WO92/18164, WO96/09814 and WO96/18388. These spray-drying and associated particle manipulation processes enable the production of soluble protein microcapsules with defined size distribution, e.g. of up to 50 µm in diameter. For example, as described in those documents, the microparticles may be produced reproducibly, e.g. with 90% or more (by volume) up to 30 µm, e.g. 10 to 20 µm, in size.

Microparticles of the invention are preferably prepared by spray-drying. Typically, a 2-fluid nozzle is used which utilises compressed air during the atomisation process; this results in the production of hollow microparticles. The maximum particle size (X50) of microparticles that can be manufactured using this atomisation system on the Niro Mobile Minor spray dryer is ~30 µm. Preferred X50 values for the micoparticles of the invention are between 5 and 50 microns, most preferably between 10 and 20 microns.

Microparticles of the invention may be prepared by spray-drying a solution of the active component with trehalose alone. An alternative procedure comprises co-spray-drying, in which fibrinogen or thrombin and another wall-forming material are formulated and spray-dried, to give microparticles in which the active component is incorporated in the wall of the particle. The product is preferably amorphous or in the form of a glass, as measured by a suitable technique such as FTIR or DSC., with a glass transition temperature of at least 50 Celsius, most preferably at least 80 Celsius.

The fibrinogen or thrombin may be full-length or any active fragment thereof. Fragments are known; see Caller et al, J. Clin. Invest. 89:546-555 (1992). Fibrinogen raw material may be a frozen solution, although, lyophilised powder which requires reconstitution prior to spray-drying may be used.

Suitable other proteins may be naturally occurring or recombinant. They may act as "wall-forming materials", as described in WO92/18164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and trehalose. Other suitable substitutes for HSA include surfactants, such as Tween 20, Tween 80, Poloxamer 407 or Poloxamer 188.

Calcium ion, e.g. as calcium chloride, may be incorporated in the thrombin feedstock. Alternatively, calcium chloride may be added to the microcapsules after processing.

Microparticles of the invention may be sterilised, if necessary or desired. Sterile processing, electron beam irradiation, γ-irradiation and ethylene oxide are examples of suitable techniques.

Although the components of the microcapsules in a fibrin sealant of the invention are preferably water-soluble, and the microparticles are preferably obtained by spray-drying a suitable solution, the microparticles that are obtainable may be free-flowing, discrete and substantially anhydrous, with a residual moisture content preferably no greater than 5% w/w, most preferably no greater than 3% w/w. This means that the compounds of fibrin sealant in accordance with this invention are not activated until they are wetted, e.g. by coming into contact with liquid at a wound site. The active components may therefore be delivered as a dry mixture, although separate application of the different microparticles is also envisaged.

A dry powder fibrin sealant product may be of particular value where application to a large surface area is required. This includes surgery and repair of traumatic injuries to various organs such as the liver and spleen. A further advantageous application is in skin grafting for burns patients, and specifically where skin epidermal sheets are cultured in vitro and then transferred to the wound site. The use of fibrin sealant in the latter indication may be particularly effective in patients with extensive burns, providing a biocompatible anchorage for skin grafts. It may also be suitable in the treatment of topical ulcers.

The following Examples illustrate the invention.

EXAMPLE 1

Spray-dried fibrinogen microparticles were prepared by dissolving 73.8 g human fibrinogen in 1650 mL water containing 275.1 g trehalose dihydrate. The resultant solution was spray-dried on a Niro Mobile Minor spray dryer using the following operating parameters:

| | |
|---|---|
| Inlet temperature: | 160° C. |
| Atomisation type: | 2 - Fluid Nozzle |
| Liquid insert: | 0.5 mm |
| Atomisation pressure: | 0.5 bar |
| Feed rate: | 18 g/minute |

The spray-dried powder had a particle size (X50, geometric diameter) of 18.4 μm and a fibrinogen content of 152 mg/g. The moisture content (Karl-Fischer) was 2%.

Spray-dried thrombin microparticles were prepared by dissolving 751,230 IU human thrombin in 1653 mL water containing 11.5 g calcium chloride dihydrate and 507.3 g trehalose dihydrate. The resultant solution was spray-dried on a Niro Mobile Minor spray dryer using the following operating parameters:

| | |
|---|---|
| Inlet temperature: | 160° C. |
| Atomisation type: | 2 - Fluid Nozzle |
| Liquid insert: | 0.5 mm |
| Atomisation pressure: | 0.5 bar |
| Feed rate: | 18 g/minute |

The spray-dried powder had a particle size (X50, geometric diameter) of 12.5 μm and a thrombin content of 977 IU/g. The moisture content (Karl-Fischer) was 3%.

The two spray-dried powders were blended in a 1:1% w/w ratio using a drum mixer at 18 rpm for 15 minutes. The resultant blend had a particle size of 15.5 μm, and a fibrinogen content of 69.1 mg/g.

Figure 2:
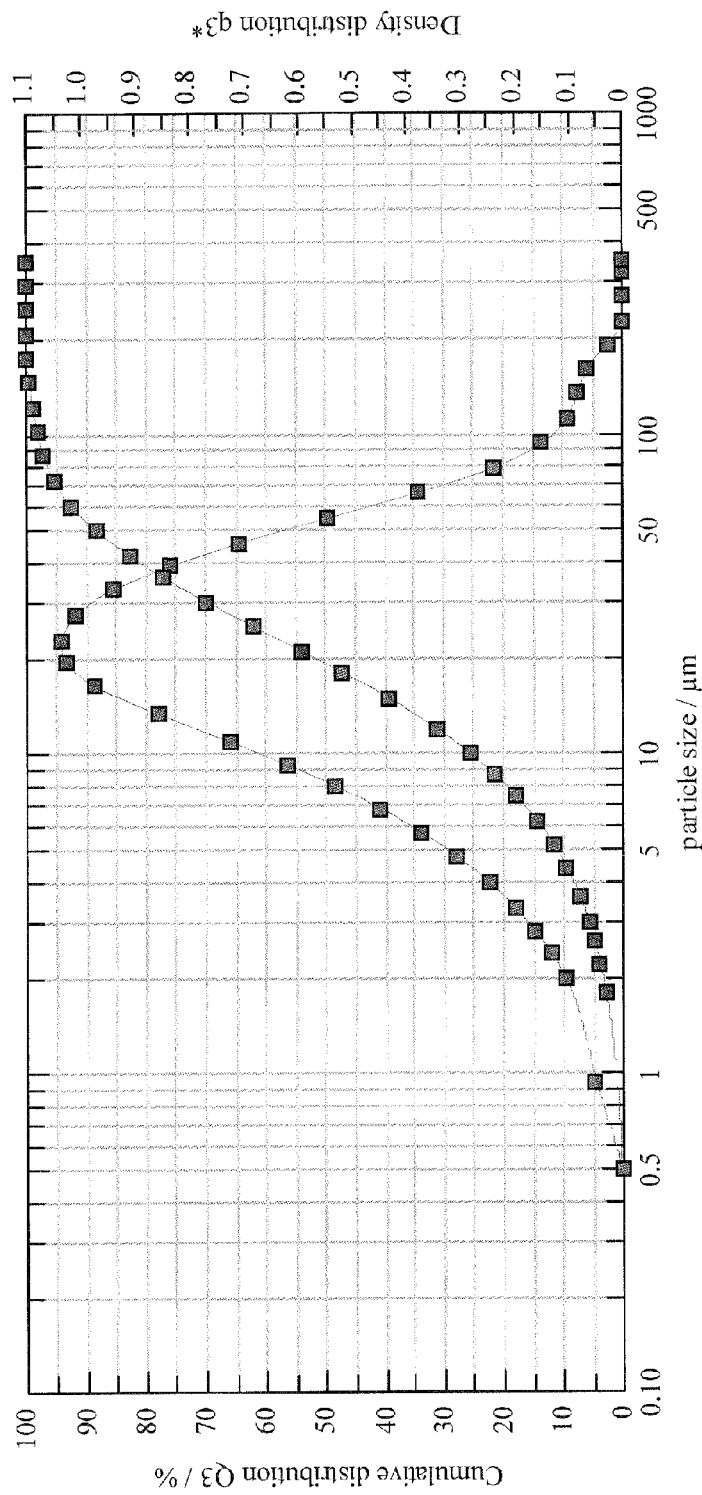
FIG. 2 is a plot of the particle size distribution of spray-dried fibrinogen:trehalose according to the invention.

The respective particle size distributions are shown in FIGS. 1 and 2.

FIG. 1 shows the cumulative distribution as follows:

| $x_0$/μm | $Q_3$/% |
|---|---|
| 1.80 | 6.71 |
| 2.20 | 8.45 |
| 2.60 | 10.02 |
| 3.00 | 11.48 |
| 3.60 | 13.58 |
| 4.40 | 16.36 |
| 5.20 | 19.25 |
| 6.20 | 23.15 |
| 7.40 | 28.33 |
| 8.60 | 33.97 |
| 10.00 | 40.87 |
| 12.00 | 50.65 |
| 15.00 | 64.07 |
| 18.00 | 75.17 |
| 21.00 | 83.61 |
| 25.00 | 91.27 |
| 30.00 | 96.53 |
| 36.00 | 99.11 |
| 42.00 | 99.85 |
| 50.00 | 100.00 |
| 60.00 | 100.00 |
| 72.00 | 100.00 |
| 86.00 | 100.00 |
| 102.00 | 100.00 |
| 122.00 | 100.00 |
| 146.00 | 100.00 |
| 174.00 | 100.00 |
| 206.00 | 100.00 |
| 246.00 | 100.00 |
| 294.00 | 100.00 |
| 350.00 | 100.00 |

| | |
|---|---|
| Evaluation: | |
| WINDOX 5.1.2.0, HRLD | Product: Fibrocaps |
| Revalidation: | Density: 1.00 g/cm³, shape factor: 1.00 |
| Reference measurement: | Disp. Meth: Set up for Fibrocaps R/M |
| 08-20 11:42:05 | $C_{opt}$ = 1.56% |
| Contamination: 0.00% | |

| Trigger condition: Fibrocaps | User parameters: |
|---|---|
| Time base: 200.00 ms | Batch Number: PV Thrombin |
| Start: c.opt >= 0.2% | Formulation: EM/08/126 |
| Valid: always | Name: aks |
| Stop: 2.000 s c.opt <= 0.2% or 10000 s real time | Run Number: Run 1 |

FIG. 2 shows the cumulative distribution as follows:

| $x_0$/μm | $Q_3$/% |
|---|---|
| 1.80 | 2.68 |
| 2.20 | 3.58 |
| 2.60 | 4.53 |
| 3.00 | 5.52 |
| 3.60 | 7.06 |
| 4.40 | 9.19 |
| 5.20 | 11.39 |
| 6.20 | 14.20 |
| 7.40 | 17.63 |
| 8.60 | 21.10 |
| 10.00 | 25.15 |

| $x_0/\mu m$ | $Q_3/\%$ |
|---|---|
| 12.00 | 30.88 |
| 15.00 | 39.17 |
| 18.00 | 46.85 |
| 21.00 | 53.70 |
| 25.00 | 61.53 |
| 30.00 | 69.48 |
| 36.00 | 76.91 |
| 42.00 | 82.47 |
| 50.00 | 87.80 |
| 60.00 | 92.11 |
| 72.00 | 95.07 |
| 86.00 | 96.87 |
| 102.00 | 97.94 |
| 122.00 | 98.72 |
| 146.00 | 99.34 |
| 174.00 | 99.81 |
| 206.00 | 100.00 |
| 246.00 | 100.00 |
| 294.00 | 100.00 |
| 350.00 | 100.00 |

| | |
|---|---|
| Evaluation: WINDOX 5.1.2.0, HRLD | Product: Fibrocaps |
| Revalidation: Reference measurement: 08-29 13:35:41 Contamination: 0.00% | Density: 1.00 g/cm³, shape factor: 1.00 Disp. Meth: Set up for Fibrocaps R/M $C_{opt}$ = 7.30% |

| Trigger condition: Fibrocaps | User parameters: |
|---|---|
| Time base: 200.00 ms | P1: SD Fibrinogen: trehalose clinical |
| Start: c.opt >= 0.2% | P2: EM/08/129 |
| Valid: always | P3: TR |
| Stop: 2.000 s c.opt <= 0.2% or 10000 s real time | P4: run 1 |

EXAMPLE 2

Four batches of microparticles were produced, using the following formulations and a Mini spray dryer, 200 mg/ml trehalose-200 units/ml thrombin 200 mg/ml sucrose-200 units/ml thrombin-1% HSA w-v 200 mg/ml trehalose-40 mg/fibrinogen 200 mg/ml sucrose-40 mg/ml fibrinogen.

The spray-drying parameters were selected so as to produce particles in the region of 10 μm.

Thrombin Formulation:

| | |
|---|---|
| Inlet temperature | 130° C. |
| Outlet temperature | ~80° C. |
| Atomisation airflow | 5 liter-min |
| Drying airflow: | 5 liter-sec |
| Feed Rate: | 5.0 g-min |

Fibrinogen Formulation:

| | |
|---|---|
| Inlet temperature: | 130° C. |
| Outlet temperature: | ~83° C. |
| Atomisation Airflow: | 15 liter-sec |

-continued

| | |
|---|---|
| Drying airflow: | 5 liter-sec |
| Feed Rate: | 3.0 g-min |

Each of the microcapsules batches was aliquoted into clear 10 ml glass vials both as separate components and as excipient-matched blends. A stability study at 4° C. was conducted over four weeks. Four timepoints were selected; initial, 1 week, 2 weeks and 4 weeks, and the following assays were employed to compare the effect of the different excipients on the stability and bioactivity retention.

Fibrinogen Analysis used a polyconal antibody to human fibrinogen as a capture antibody and a second peroxidise-labelled antibody to human fibrinogen is used for detection in a chromogenic assay.

Thrombin Analysis was based on a commercial substrate which is sensitive to thrombin and gives a colour change which can be measured. The initial rate of change in absorbance is proportional to thrombin concentration.

Particle Size was measured using a LS230 Laser Sizer in conjunction with Medium Chain Trigylceride oil to determine the particle size of the spray dried material.

Thermogravimetric Analysis was carried out to assess moisture content.

Flow time was the time taken for a microcapsule blend to pass through a funnel of a pre-determined size was used as a comparative measure of flowability between batches.

Angle of Repose indicates the flowability of a powder and was measured by the calculation of the angle created upon the flow of a powder through a funnel and subsequent accumulation on a flat surface.

Packed and tap density were measured using the Jolting Volume Meter and the values used in Carrs Compressibility Index (% CCI).

Clot Strength utilises the formulation of a clot from a blend in a plastic syringe. A bead is suspended in the syringe prior to clot formation and the weight required to pull the bead through the clot is recorded.

Adhesive Strength: blends are applied to a piece of rat skin via a 10 ml glass pipette fitted with a compressed air supply. The weight required to separate two pieces of the tissue bonded together by a blend is used as a measurement of adhesive strength. (This assay is based on a Gottlob skin test method—Gesting and Lerner: Autologous fibrinogen for tissue adhesion haemostatis (1983)).

Additional assays were performed at the four week timepoint; SDS PAGE to assess the effects of spray-drying on the structural integrity of the bioactives and a BCA assay for total protein determination. Scanning electron micrographs (SEM) were also obtained for each of the individual formulations.

Results demonstrated no significant changes over the stability period for either formulation, but the data do suggest a greater retention of activity generated for the trehalose formulation when compared with the sucrose formulation. The clot strength values also indicate an increased activity retention with the trehalose formulation. The addition of HSA to the trehalose-thrombin formulation showed no significant differences in bioactivity retention compared to the trehalose-thrombin formulation. The flow properties were retained over the stability period which is reflected in the consistent adhesive strength values.

SDS PAGE data demonstrated the retention of structural integrity post-spray-drying.

Scanning electron micrographs revealed similar morphology for all formulations.

Dry heat viral inactivation step was conducted for 72 hours at 80° C.

The individual fibrinogen and thrombin components were assessed using ELISA and chromogenic assays respectively and the blends were analysed using the clot strength assay. The results are documented in Table 1.

TABLE 1

Dry Heat Sterilisation

| Sample | Bioactivity - Concentration per 100 mg spray-dried Product | Clot Strength (g) |
|---|---|---|
| Trehalose - Thrombin microcapsules | 101.6 units (97%) | * |
| Trehalose - Fibrinogen microcapsules | 14.17 mg (103%) | * |
| Trehalose - Active blend | * | 64.8 g |
| Sucrose - Thrombin microcapsules | 93.8 units (89%) | * |
| Sucrose - Fibrinogen microcapsules | 11.04 mg (80.5) | * |
| Sucrose - Active blend | * | 62.7 g |

Theoretical thrombin concentration=105 units-100 mg spray-dried product
Theoretical fibrinogen concentration=13.7 mg-100 mg spray-dried product
% Retention is shown in brackets Expected clot strength=~70 g The bioanalytical results indicate the excipient trehalose allows a greater retention of the active during the dry heat step.

Gamma-irradiation employed 25 kGy at a rate of 8 kGy/hour. Samples were exposed to these irradiation conditions both as separate components and as a blend.

The components were assessed using ELISA and chromogenic assays respectively and the blends examined via the clot strength assay. The results are documented in Table 2.

TABLE 2

| Gamma Irradiation Sterilisation | | |
|---|---|---|
| Sample | Bioactivity - Concentration per 100 mg spray-dried Product | Clot Strength (g) |
| Trehalose - Thrombin microcapsules | 71 units (71%) | * |
| Trehalose - Fibrinogen microcapsules | 10.3 mg (73%) | * |
| Trehalose - Active blend | * | 59.5 g |
| Sucrose - Thrombin microcapsules | 71 units (71%) | |
| Sucrose - Fibrinogen microcapsules | 7.7 mg (55.5 %) | * |
| Sucrose - Active blend | * | 36.9 g |

% Retention is shown in brackets.

The conditions investigated in the terminal sterilisation study (72 hours at 80° C.) suggest that trehalose offers a higher level of protection to the protein, as reflected by the activity retention. This observation may also suggest a trehalose formulation may be capable of room temperature storage. Gamma irradiation of the sucrose formulation resulted in a 50% drop in fibrinogen activity. The trehalose formulation was found to have a significantly higher fibrinogen activity retention (70%) as measured by the ELISA and clot strength assays.

What is claimed is:

1. A dry powder fibrin sealant composition, comprising:
- a mixture of first microparticles that comprise fibrinogen and trehalose, and
- second microparticles that comprise thrombin and trehalose,
- wherein trehalose is the only stabilizing sugar in the first microparticles and second microparticles, and
- wherein the concentration of trehalose in the first microparticles is sufficient to preserve at least 70% of fibrinogen activity after exposure of the first microparticles to a 25 kGy dose of gamma irradiation delivered at a rate of 8 kGy/hour.

2. The composition of claim 1, wherein fibrinogen activity is measured by ELISA.

3. The composition of claim 1, wherein fibrinogen activity is measured by clot strength assay.

4. The composition of claim 1, wherein fibrinogen activity is measured by ELISA and clot strength assay.

5. The composition of claim 1, wherein the concentration of trehalose in the first microparticles and second microparticles is sufficient to preserve at least 70% of expected clot strength after exposure of the mixture of microparticles to a 25 kGy dose of gamma irradiation delivered at a rate of 8 kGy/hour.

6. The composition according to claim 1 or claim 5, wherein said first microparticles contain 0.5 to 20% w/w fibrinogen.

7. The composition of claim 6, wherein said second microparticles comprise 10 to 20,000 IU/g thrombin.

8. The composition of claim 7, wherein said second microparticles comprise 25 to 1,000 IU/g thrombin.

9. The composition of claim 1 or 5, wherein said microparticles are spray-dried microparticles.

10. The composition of claim 9, wherein the composition has a residual moisture content no greater than 5% (w/w).

11. The composition of claim 10, wherein the residual content is no great than 3% (w/w).

12. The composition of claim 1 or claim 5, wherein said first and second microparticles are mixed in a weight ratio of 1:1.

13. A method of treating a wound, comprising administering to the wound an effective amount of the composition as defined in claim 1.

14. The method, as claimed in claim 13, further comprising the step of applying pressure immediately after said administering.

15. The dry powder fibrin sealant composition of claim 1, wherein the composition is sterilizable.

16. A method for preparing a dry powder fibrin sealant composition comprising a mixture of first microparticles that comprise fibrinogen and trehalose and second microparticles that comprise thrombin and trehalose, wherein trehalose is the only stabilizing sugar in the first microparticles and second microparticles, the method comprising:
- (i) spray-drying a first aqueous solution comprising fibrinogen and trehalose to produce said first microparticles, wherein said first aqueous solution does not include a second stabilizing sugar and the concentration of trehalose in the first microparticles is sufficient to preserve at least 70% of fibrinogen activity after exposure of the first microparticles to a 25 kGy dose of gamma irradiation delivered at a rate of 8 kGy/hour;

(ii) spray-drying a second aqueous solution comprising thrombin and trehalose to produce said second microparticles, wherein said second aqueous solution does not include a second stabilizing sugar; and (iii) mixing the first and second microparticles.

17. The method of claim 16, wherein the concentration of trehalose in each of the first and second microparticles is sufficient to preserve at least 70% of expected clot strength after exposure of the mixture of microparticles to a 25 kGy dose of gamma irradiation delivered at a rate of 8 kGy/hour.

18. The method of claim 16 or claim 17, wherein said first microparticles contain 0.5 to 20% w/w fibrinogen.

19. The method of claim 16 or claim 17, wherein said second microparticles comprise 10 to 20,000 IU/g thrombin.

20. The method of claim 19, wherein said second microparticles comprise 25 to 1,000 IU/g thrombin.

21. The method of claim 16 or claim 17, wherein each of the first and second aqueous solutions is spray-dried with an outlet temperature of at least about 80° C.

22. The method of claim 21, wherein the dry powder fibrin sealant composition has a residual moisture content no greater than 5% (w/w).

23. The method of claim 22, wherein each of the first and second aqueous solutions is spray-dried with an outlet temperature of at least about 83° C.

24. The method of claim 22, wherein the residual moisture content is no greater than 3% (w/w).

25. The method of claim 16 or claim 17, wherein step (iii) comprises mixing the first and second microparticles in a weight ratio of 1:1.

* * * * *